United States Patent
Li et al.

(10) Patent No.: US 10,339,673 B2
(45) Date of Patent: Jul. 2, 2019

(54) DUAL-ENERGY RAY IMAGING METHODS AND SYSTEMS

(71) Applicants: Tsinghua University, Beijing (CN); NUCTECH COMPANY LIMITED, Beijing (CN)

(72) Inventors: Liang Li, Beijing (CN); Zhiqiang Chen, Beijing (CN); Kejun Kang, Beijing (CN); Li Zhang, Beijing (CN); Ziran Zhao, Beijing (CN); Yuxiang Xing, Beijing (CN); Yongshun Xiao, Beijing (CN); Jianping Gu, Beijing (CN); Juan Zheng, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 15/129,455

(22) PCT Filed: Dec. 23, 2015

(86) PCT No.: PCT/CN2015/098470
§ 371 (c)(1),
(2) Date: Sep. 27, 2016

(87) PCT Pub. No.: WO2016/107480
PCT Pub. Date: Jul. 7, 2016

(65) Prior Publication Data
US 2017/0309043 A1    Oct. 26, 2017

(30) Foreign Application Priority Data
Dec. 30, 2014    (CN) .......................... 2014 1 0842363

(51) Int. Cl.
  G01N 23/04    (2018.01)
  G06T 11/00    (2006.01)
  G06T 7/00     (2017.01)

(52) U.S. Cl.
  CPC ............ G06T 11/003 (2013.01); G01N 23/04 (2013.01); G06T 7/0002 (2013.01);
  (Continued)

(58) Field of Classification Search
  CPC ..... G06T 11/003; G06T 11/008; G06T 7/002; G06T 2207/30112; G06T 2211/408;
  (Continued)

(56) References Cited

U.S. PATENT DOCUMENTS 6,198,795 B1 * 3/2001 Naumann ............ G01V 5/0041
                                                    378/57
2010/0172464 A1   7/2010 Pavlovich et al.
2010/0290691 A1 * 11/2010 Eilbert ................ G01V 5/0033
                                                    382/132

FOREIGN PATENT DOCUMENTS

CN    101435783 A    5/2009
CN    101647706 A    2/2010
(Continued)

OTHER PUBLICATIONS

International Search Report dated Mar. 22, 2016 for International application No. PCT/CN2015/098470.
(Continued)

Primary Examiner — Courtney D Thomas
(74) Attorney, Agent, or Firm — Morgan, Lewis & Bockius LLP

(57) ABSTRACT

Disclosed is a dual-energy ray imaging method and system. The method comprises: calculating the mass thicknesses of the materials in the overlapped area of two materials by using a calibrated surface fitting method, and then decom-
(Continued)

posing a pair of original high-energy and low-energy data for this pixel into two high-low-energy data sets corresponding to the two materials, and finally calculating and acquiring the composition result of different materials for each pixel. The disclosure is especially advantageous in that the problem of error recognition of materials due to the two overlapped materials can be eliminated and the stratified imaging of multiple materials can be achieved, thereby improving the accuracy of the substance recognition and reducing the rate of false positive and false negative which is very important to the applications in the field of security check and anti-smuggling.

11 Claims, 9 Drawing Sheets

(52) U.S. Cl.
CPC .. *G06T 11/008* (2013.01); *G06T 2207/10081* (2013.01); *G06T 2207/30112* (2013.01); *G06T 2211/408* (2013.01)

(58) Field of Classification Search
CPC ........ G06T 2207/10081; G06T 7/0002; G01V 5/0041; G01N 2223/206; G01N 23/04; G01N 23/087
See application file for complete search history.

(56) References Cited

FOREIGN PATENT DOCUMENTS

| | | |
|---|---|---|
| EP | 1 970 731 A2 | 9/2008 |
| JP | 2010-091483 A | 4/2010 |
| WO | 2009/044658 A1 | 4/2009 |
| WO | 2009/152506 A1 | 12/2009 |

OTHER PUBLICATIONS

Supplementary European Search Report dated Oct. 10, 2018 in corresponding EP Application No. 15875158.6.

* cited by examiner

DUAL-ENERGY RAY IMAGING METHODS AND SYSTEMS

TECHNICAL FIELD

Embodiments of the present disclosure relates to radiation imaging, and in particular, to dual-energy ray imaging methods and systems.

BACKGROUND

Since the X-ray is discovered, the X-ray radiography technology has been widely used as a non-destructive inspection measure in the medical, security, anti-smuggling, and many other fields. The development of the X-ray radiography technology is begun with the initial X-ray film photography to CR (Computed Radiography), then to DR (Digital Radiography), to dual-energy spectrum DR imaging, and even to multi-energy spectrum DR imaging technology. The basic principle of the X-ray radiography technology may be described as follows. An X-ray is emitted to an object to be inspected and interacted with the material of the object. The X-ray attenuated after passing through the object to be inspected is received by a detector and converted into an electronic signal to form an image. Magnitude of signal strength of each pixel in the image reflects the degree of absorption of the X-photons by the material in the direction of the X-ray transmission for this pixel, that is, the integral of the X-ray linear attenuation coefficients for all materials in the direction of the X-ray transmission path. Therefore, a mono-energy spectrum radiography cannot directly provide material information, such as density of the object to be inspected or atomic number, and the shape information of each object in the image is usually required for determining the object to be inspected. However, the shape information is often inaccurate, especially for materials without a fixed shape, such as explosives, drugs, gasoline, etc., resulting in a false positive or a false negative.

Due to the above limit in the mono-energy spectrum radiography, the need of accurate recognition of the object material cannot be met and the dual-energy radiography technology is proposed. Unlike the mono-energy spectrum radiography, a dual-energy radiography system uses two sets of radiographic images with different energy spectrums and uses a dedicated algorithm for material recognition which may achieve recognition of specificity of different substances or materials. Such a recognition cannot be achieved by the mono-energy spectrum radiography technology.

The interactions between the X-ray photons and the substance are typically divided into three categories: the photoelectric effect, the Compton scattering, and the electron pair effect, and the reaction cross-sections for the three categories of interactions are related to the X photon energy and atomic number of the substance. For a given substance, its X-ray linear attenuation coefficient is equal to the product of the total atomic cross-section and the atomic density. Therefore, by measuring the X-ray linear attenuation coefficient of the substance under different energy spectrums, the atomic number of the substance and the electron density can be determined by using the relation between the X-ray linear attenuation coefficient and the total atomic cross-section, and the recognition of the material is thus achieved.

The current dual-energy radiographic system typically uses a dual-energy curve based method for material recognition to calculate the atomic number quickly and accurately, and a qualitative and quantitative evaluation of the material is achieved based thereon. Based on different application requirements, the existing dual-energy radiography technology may be divided into two different categories of low-energy dual-energy and high-energy dual-energy:

1) the low-energy dual-energy typically refers to a case where the maximum X-ray photon energy <=450 keV where the interactions between the X-ray photons and the substance have only two categories: the photoelectric effect and the Compton scattering. In the low energy region, the photoelectric effect is dominant and related to Z intensity; and in the medium low region, the Compton scattering is dominant and basically not related to Z. The ratio of the attenuation coefficients under the two energies is changed monotonically with Z, resulting in a better discrimination. The material recognition can be achieved based on this ratio. The low-energy dual-energy radiography technology is typically applied to cases where the object has a smaller volume and a rather lower density, such as luggage item machine, absorptiometry, coal ash analyzer, etc.

2) the high-energy dual-energy typically refers to a case where the maximum X-ray photon energy >=1 MeV where the interactions between the high-energy X-ray photons and the substance are different from those for the low-energy photons: the three categories of interactions, i.e. the photoelectric effect, the Compton scattering and the electron pair effect, coexist. Therefore, their methods for implementing material recognition and their capabilities of recognition are different. In general, in the MeV energy region, due to a small gap between high-low energy curves for different substances, its material recognition capability is weaker than that for low-energy dual-energy case. The high-energy radiography is typically applied to inspection of material having a high atomic number which cannot be penetrated by the low-energy X-ray or inspection of an object having a large volume, such as, inspection of radioactive materials, large container inspection system, the flight case inspection system, and non-destructive testing of large metal parts, or the like.

However, the above currently widely used dual-energy radiography technology still has its inherent drawbacks. Since in the radiography the X-ray transmissive scanning is performed on the object at a certain view angle only, the acquired high-low energy projection data is representative of integral information of all materials on each X-ray straight propagation path. Therefore, when there are multiple kinds of materials on this path, the dual-energy radiography cannot distinguish such an overlapping relation of materials located front and rear. In other words, the dual-energy radiography can only recognize a single material (pure substance) correctly without any overlapping relation. For cases where two or more kinds of materials are presented in the direction of X-ray transmission with an overlapping relation, the existing dual-energy DR imaging technology cannot distinguish them and can only recognize it as a new mixed material, resulting in an inaccurate recognition of the original materials and therefore an error in recognition. This drawback also imposes a limit to the value of the dual-energy X-ray DR imaging technology in the field of security inspection.

To solve the problem of correctly recognizing the overlapped materials, the prior art typically tries to avoid the overlapped areas as much as possible by using multiple additional view angles and capturing the dual-energy radiographic images at different angles; however, this method cannot guarantee that the problem can be solved completely. Another solution is to use a more complicated CT (computed tomography) technology to capture radiographic images at hundreds or thousands of angles throughout a range of 360°. For example, a dedicated CT reconstruction algorithm is used for direct calculation to acquire a full 3D image information of the object, and the problem of overlapped substance is solved fundamentally. However, both of the hardware of the imaging system in the above two solutions are to be changed greatly, especially for the CT technology. This will greatly increase the hardware cost and technical problem of the dual-energy imaging system, and also increase the difficulty in maintenance of the system and reduce its application scope.

SUMMARY

In view of the above one or more problems of the prior art, a dual-energy ray imaging method and system are proposed to eliminate the problem of false recognition due to materials overlapped in the ray direction.

In an aspect of the present disclosure, a dual-energy ray imaging method is proposed, the method including the steps of: performing a dual-energy transmissive scanning on an object to be inspected to acquire high-energy projection data and low-energy projection data for at least a part of the object to be inspected; calculating mass thicknesses of two base materials corresponding to at least one group of projection data composed of the high energy projection data and the low energy projection data for each pixel by using a calibrated surface fitting method, the two base materials comprising a first base material and a second base material; calculating a first high and low energy data set corresponding to the first base material and a second high and low energy data set corresponding to the second base material based on respective mass attenuation coefficients and the calculated mass density of the two base materials; and performing a substance recognition by using the first high and low energy data set and second high and low energy data set which are calculated.

Preferably, the method further includes a step of: determining whether the high energy projection data and low energy projection data for at least a part of the object to be inspected correspond to a combination of the two base materials by using a lookup table of single base materials; wherein the mass thicknesses of the two base materials are calculated when the result of the determination is yes.

Preferably, the high energy projection data and the low energy projection data are brought into the lookup table of single base materials to determine their positions in high and low energy curves of single pure materials with different thicknesses, and then to determine whether the positions correspond to the two base materials by calculating distances from the positions to the curves for different base materials.

Preferably, the method further includes the steps of displaying an image of the object to be inspected based on at least one of the high energy projection data and the low energy projection data; and receiving a user selection of at least part of the image to acquire an area of interest; wherein the mass thicknesses of the two base materials are calculated with respect to the area of interest.

Preferably, the step of calculating mass thicknesses of two base materials by using a calibrated surface fitting method includes: searching a high and low energy projection database for corresponding mass thicknesses of the two base materials by using the high energy projection data and the low energy projection data.

Preferably, one of the R-curve method, the high and low energy curve method, or the α curve method is used for substance recognition.

Preferably, a formula for calculating mass thicknesses for different base materials is acquired by a quadratic surface fitting.

In another aspect of the present disclosure, a dual-energy ray imaging system is proposed, the system including: a scanning device configured to perform a dual-energy transmissive scanning on an object to be inspected to acquire high energy projection data and low energy projection data for at least a part of the object to be inspected; a data processing device configured to calculate mass thicknesses of two base materials corresponding to at least one group of projection data composed of the high energy projection data and the low-energy projection data for each pixel by using a calibrated surface fitting method, the two base materials comprising a first base material and a second base material, further configured to calculate a first high and low energy data set corresponding to the first base material and a second high and low energy data set corresponding to the second base material based on respective mass attenuation coefficients and the calculated mass density of the two base materials; and configured to perform a substance recognition by using the first high and low energy data set and second high and low energy data set which are calculated.

Preferably, the dual-energy ray imaging system further comprises: a display device configured to display an image of the object to be inspected based on at least one of the high energy projection data and the low energy projection data; and an input device configured to receive a user selection of at least part of the image to acquire an area of interest; wherein the mass thicknesses of the two base materials are calculated with respect to the area of interest.

Preferably, the data processing device searches a high and low energy projection database for corresponding mass thicknesses of the two base materials by using the high-energy projection data and the low energy projection data.

The solutions of the above embodiments may eliminate the problem of error recognition of materials and achieve the stratified imaging of multiple materials, thereby improving the accuracy of the substance recognition and reducing the rate of false positive and false negative which is very important to the applications in the field of security check and anti-smuggling.

BRIEF DESCRIPTION OF THE DRAWINGS

To understand the present disclosure in a better way, a detailed description of the present disclosure will be given with reference to the following drawings, in which.

DETAILED DESCRIPTION

Specific embodiments of the present disclosure will be described in detail below and please note that the embodiments described herein are used for the purpose of exemplification rather than limitation of the present disclosure. Hereinafter, to provide a thorough understanding of the present disclosure, numerous specific details are set forth. However, it would be obvious for one ordinarily skilled in the art that the present disclosure can be practiced without these specific details. In other examples, known structures, materials, or methods are not described in detail to avoid any possible obfuscation of the present disclosure.

Throughout the specification, the reference to "an embodiment", "the embodiment", "an example", or "the example" is meant that a specific feature, structure, or feature described with reference to this embodiment or example is contained by at least one embodiment of the present disclosure. Therefore, the phrases "in an embodiment", "in the embodiment", "an example", or "the example" throughout the specification is not necessarily intended to refer to a same embodiment or example. Further, specific features, structures, or characteristics may be combined into one or more embodiments or examples in any suitable combination and/or sub-combination. Further, it is appreciated by one ordinarily skilled in the art that the term "and/or" used herein comprises any and all combinations of one or more related items that are listed.

With regard to the problem in the prior art of false recognition due to overlapped materials in the ray direction, embodiments of the present disclosure propose a layered material based dual-energy radiography technology. According to this technology, materials intervals are first coarsely divided for each pixel data by the high-low-energy curve, and then the mass thicknesses of the materials in the overlapped area of two materials by using a calibrated surface fitting method. After that, a pair of original high-energy and low-energy data for this pixel is decomposed into two high and low energy data sets corresponding to the two materials, and finally the composition result of different materials is calculated and acquired for each pixel. This solution is advantageous in that the problem of error recognition of materials due to the two overlapped materials can be eliminated and the stratified imaging of multiple materials can be achieved, thereby improving the accuracy of the substance recognition and reducing the false rate which is very important to the applications in the field of security check and anti-smuggling. Further, this technology can be extended to a multi-energy radiography scenario, such as N-energy (energy spectrum, N>=3). At this point, the stratified imaging of N materials can be achieved on each X-ray path.

Figure 1:
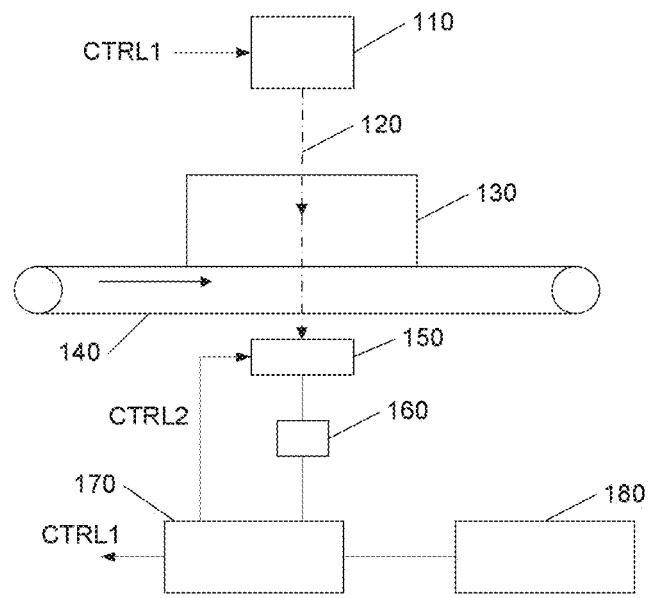
FIG. 1 is a diagram showing a dual-energy X-ray DR imaging system according to an embodiment of the present disclosure.

FIG. 1 is a structural diagram showing a dual-energy ray system according to an embodiment of the present disclosure. As shown in FIG. 1, the system includes a bearing mechanism 140 (for example, a belt) carrying forward an object to be inspected 130, an X-ray source 110, a detector module 150, a collecting circuit 160, a controller 170, and a data processing computer 180, among others. The ray source 110 includes one or more X-ray generators for performing a dual-energy scanning. The plurality of X-ray generators are distributed on one or more planes which intersect with the travelling direction of the object to be inspected 130.

As shown in FIG. 1, the luggage to be inspected 130 is carried by the bearing mechanism 140 to pass through the scanning area between the ray source 110 and the detector 150. In some embodiments, the detector 150 and the collecting circuit 160 may be, for example, a detector-and-data-collector with an integrated modular structure, such as a multiple-row detector, for detecting rays transmitted through the object to be inspected such that analog signals are acquired and converted into digital signals, thereby outputting projection data of the object to be inspected with respect to X-ray. For example, a row of detectors are arranged for high-energy rays and another row of detectors are arranged for low-energy rays, or a same row of detectors are used in a time division manner for high-energy and low energy rays. The controller 170 is used for controlling various parts of the whole system to operate synchronously. The data processing computer 180 is used for processing the data collected by the data collector, processing and reconstructing the data, and outputting the result.

According to this embodiment, the detector 150 and the collecting circuit 160 are used for acquiring transmission data of the object to be inspected 130. The collecting circuit 160 comprises a data amplification shaping circuit which may operate in a (current) integration manner or a pulse (courting) manner. A data output cable of the collecting circuit 150 is coupled to the controller 170 and the data processing computer 180, and stores the collected data into the data processing computer 180 based on a trigger command.

In some embodiments, the detector module 150 comprises multiple detecting units which receive the X-rays transmitted through the object to be inspected. The data collecting circuit 160 is coupled to the detector module 150 and converts the signals generated by the detector module 160 into the detection data. The controller 170 is coupled to the ray source 110 via a control line CTRL1, to the detector module via a control line CTRL2, and to the data collecting circuit. The controller 170 controls at least two of the X-ray generators in the ray source to generate X-rays with different energy alternately which are then emitted and pass through the object to be inspected as the object to be inspected moves. In addition, the controller 170 controls the detector module 150 and the data collecting circuit 160 to acquire detection data corresponding to the X-ray generators with at least two energy, respectively. The data processing computer 180 reconstructs the image of the object to be inspected based on the detection data.

Figure 2:
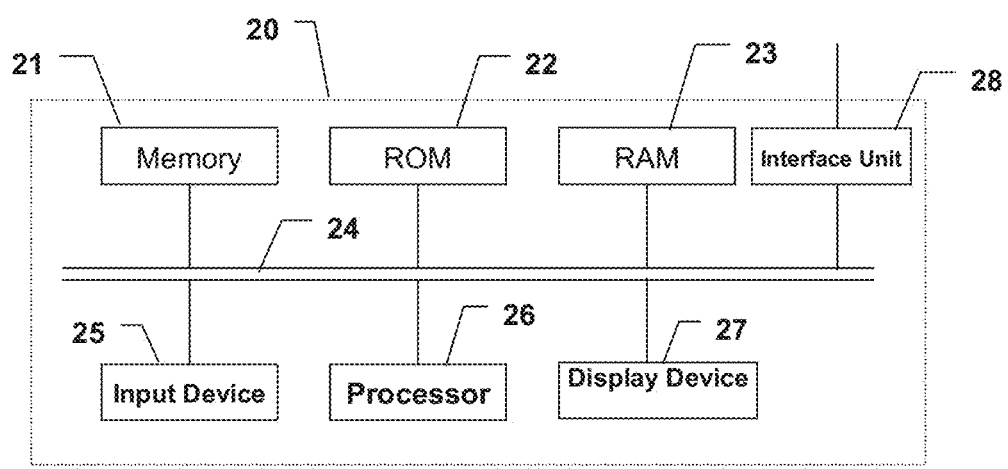
FIG. 2 is a diagram showing an internal structure of a computer for image processing in the embodiment shown in FIG. 1.
Figure 3:
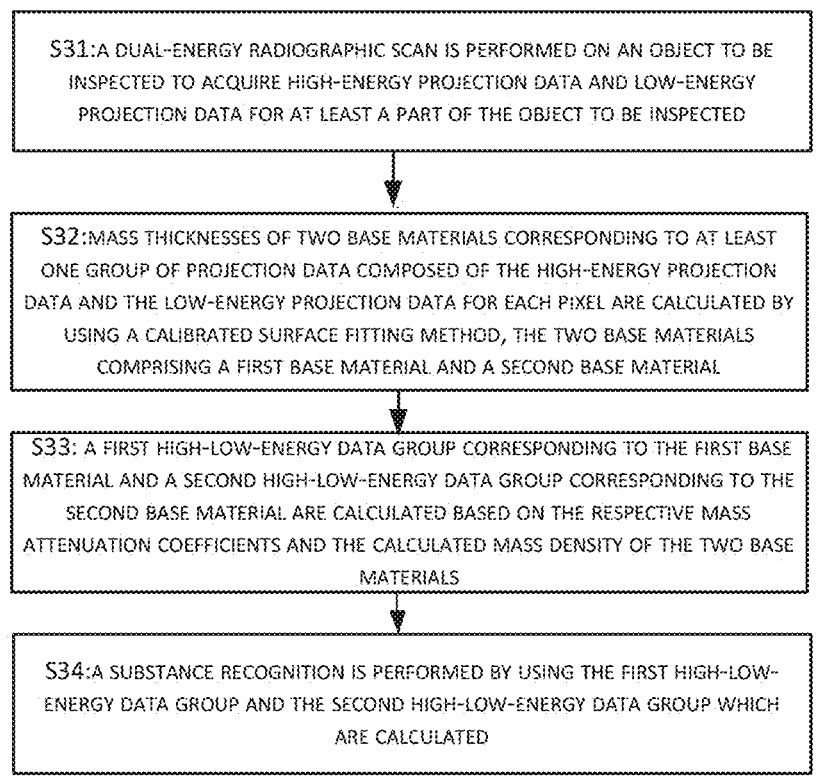
FIG. 3 is a flow chart showing a dual-energy ray imaging method according to one embodiment.

FIG. 2 is a block diagram showing the structure of the data processing computer 180 as shown in FIG. 1. As shown in FIG. 3, the data collected by the collecting circuit 160 is stored into a memory 21 via an interface unit 28 and a bus 24. Configuration information and programs for the computer data processor are stored in a Read-Only Memory (ROM) 22. A Random Access Memory (RAM) 23 is used for temporarily storing various data during the operation of a processor 26. In addition, computer programs for data processing are also stored in the memory 21. The internal bus 24 connects the above memory 21, Read Only Memory (ROM) 22, Random Access Memory (RAM) 23, an input device 25, the processor 26, a display device 27, and the interface unit 28.

After an operation command is input by a user via the input device 25, such as a keyboard, a mouse, etc., the code instructions of the computer program instructs the processor 26 to perform a predetermined data reconstruction algorithm. After the result of the data processing is acquired, it will be displayed on the display device 27, such as an LCD display, or output directly in a hardcopy form, such as printing.

For example, the ray source 110 may be a radioisotope (such as, Cobalt-60), or a low-energy X-ray machine or high-energy X-ray accelerator.

For example, in terms of material, the detector array 150 may be a gas detector, a scintillator detector, or a solid detector, etc., and in terms of array arrangement, the detector array 150 may be a single-row, double-row, or multiple-row detector array, or a single-layer detector or a double-layer high-low-energy detector, or the like.

The object delivery mechanism 140 enables the object 130 to be moved for forming a scanned image, or the object may move by itself, such as a container lorry, or equivalently the object stays still and the X-ray source and the detector array move for accomplishing the scanning process.

In order to achieve a dual-energy X-ray DR scan, three technical measures as follows are typically used: 1) the X-ray source provides two energy spectrums (high and low) by changing its voltage to finish a high and low energy X-ray DR scan; 2) a dual-layer high-low-energy detector is used to divide the incoming X-ray energy spectrum into two parts (high-energy and low-energy) to collect dual-energy X-ray DR scanned data, respectively; and 3) a dual-X-ray source and a dual-detector array are used to perform the high-energy and low-energy X-ray DR scans, respectively. All of the above technical measures are used in the field of security, anti-smuggling, and clinical medical imaging. The embodiments of the present disclosure may be applied to any of the above dual-energy X-ray imaging systems.

FIG. 3 is a flow chart showing a dual-energy ray imaging method according to one embodiment. As shown in FIG. 3, at step S31, a dual-energy radiographic scan is performed on an object to be inspected to acquire high-energy projection data and low-energy projection data for at least a part of the object to be inspected, for example, by a dual-energy radiographic system scanning the object to be inspected to acquire the high-energy projection data and low-energy projection data for the object.

At step S32, mass thicknesses of two base materials corresponding to at least one group of projection data composed of the high-energy projection data and the low-energy projection data for each pixel are calculated by using a calibrated surface fitting method, the two base materials comprising a first base material and a second base material. For example, in the image processing computer 180, the high-energy projection data and the low-energy projection data are decomposed in terms of the two base materials (for example, iron and graphite) to acquire the mass thicknesses for the two base materials.

At step S33, a first high and low energy data set corresponding to the first base material and a second high and low energy data set corresponding to the second base material are calculated based on the respective mass attenuation coefficients and the calculated mass density of the two base materials. Because the attenuation coefficients of the two base materials are known, the high energy data set and the low energy data set corresponding to these two materials are calculated, respectively, based on the calculated mass density and the known attenuation coefficients.

At step S34, substance recognition is performed by using the first high and low energy data set and the second high and low energy data set which are calculated. For example, the substance is recognized from the high and low energy data sets for different base materials, and the material layers in the ray direction are thus recognized correctly.

Figure 4:
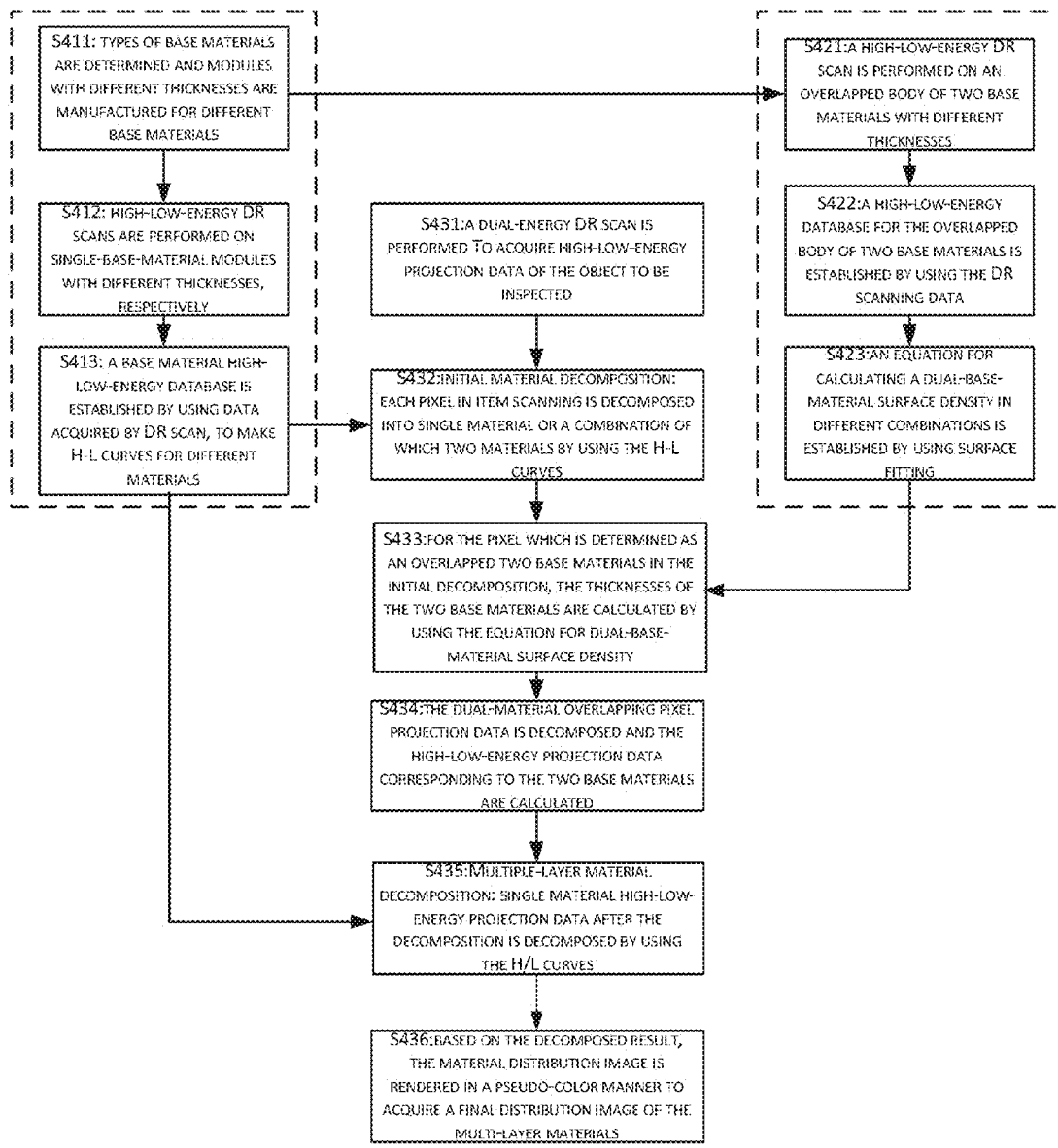
FIG. 4 is a flow chart describing a dual-energy ray imaging method according to another embodiment of the present disclosure.

FIG. 4 is a flow chart describing a dual-energy ray imaging method according to another embodiment of the present disclosure. Based on the Beer-Lambert theorem, after a beam of X-ray having a certain energy spectrum distribution passes through a single material substance having a mass thickness of M, a signal intensity collected at an energy integral detector can be described by following equation:

$$I = \int I_0(E) \cdot e^{-\mu_m(E) \cdot M} dE \quad (1)$$

where $\mu_m(E)$ denotes the mass attenuation coefficient of this material with respect to the X-ray having an energy of E; the mass thickness $M=\rho \cdot D$ is a product of density and the thickness of the object in the X-ray direction; and $I_0(E)$ denotes a signal intensity collected by the detector when photons having an energy of E in this beam of X-ray is directly incident onto the detector without passing through any object. In the X-ray imaging, the equation (1) is usually converted into following projection data:

$$p = -\ln\frac{I}{I_0} = -\ln\int D(E) \cdot e^{-\mu_m(E) \cdot M} dE \quad (2)$$

Where, $I_0$, denotes a total intensity of all signals collected by the detector when this beam of X-ray is directly incident onto the detector without passing through any object, and $D(E)=I_0(E)/I_0$ denotes a systematic energy spectrum after normalization.

In the dual-energy X-ray imaging, projection data for two different energy spectrums (high-energy and low-energy) are required to be collected, which are denoted in the embodiments of the present disclosure as:

$$p_1 = -\ln\int D_1(E) \cdot e^{-\mu_m(E) \cdot M} dE \quad (3)$$

$$p_2 = -\ln\int D_2(E) \cdot e^{-\mu_m(E) \cdot M} dE \quad (4)$$

where, $D_1(E)$ and $D_2(E)$ denote low-energy and high-energy (normalized) systematic energy spectrums, respectively.

Figure 5:
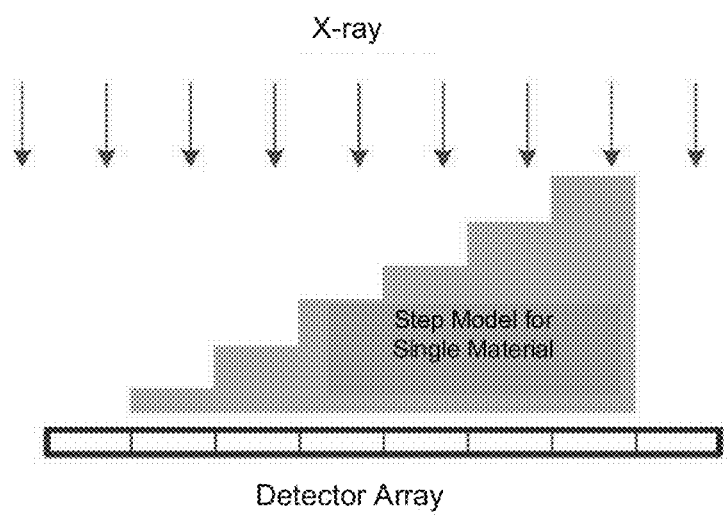
FIG. 5 is a diagram describing a step model of a single uniform material according to an embodiment of the present disclosure.

A flow chart of the method according to the technical solutions of the present disclosure is shown as FIG. 4 in which at steps S411, S412, and S413, types and number of the base materials are selected according to the requirements of the dual-energy X-ray imaging task, for example, graphite, water, aluminum, iron, lead, etc., and a step model of single uniform material is designed and made as shown in FIG. 5. In this step, each step has a uniform thickness, and the number of the steps is determined as required. In general, the more the number of steps, the more the high-low-energy data of the base materials that can be collected, and the accurate the subsequent calculation result is. The high-low-energy projection data for each step model of single material is scanned to establish a database or a lookup table for the base materials, and high-low-energy curves for different base materials are depicted.

Figure 6:
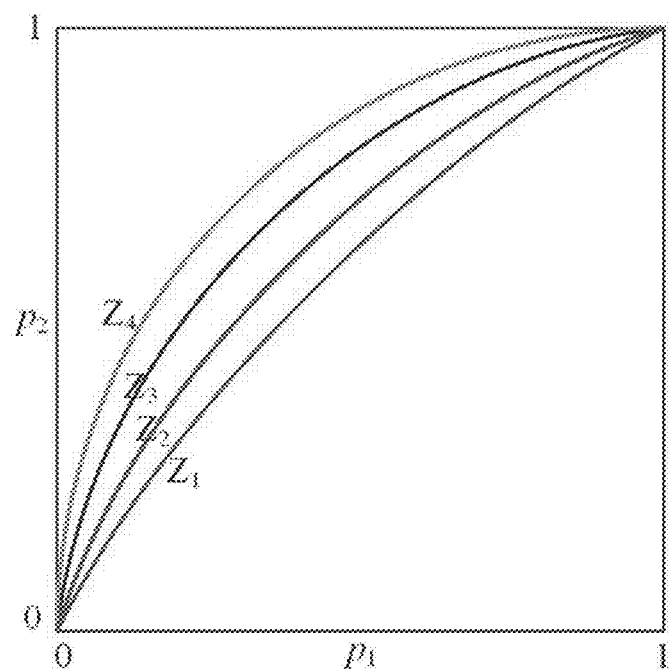
FIG. 6 is brief systematic model describing a simulated experiment for examining a calibrated method according to an embodiment of the present disclosure.

FIG. 6 shows a diagram of high-low-energy curves for different base materials where the abscissa axis represents projection data of a low-energy X-ray after passing through a base material module having a certain thickness and an atomic number of Z, and the ordinate axis represents projection data of a high-energy X-ray after passing through a base material module having a certain thickness and an atomic number of Z. The low-energy and high-energy projection data for a same base material having different thicknesses are depicted in a 2-dimension plane as shown in FIG. 6 to form a curve. Therefore, four curves in green, blue, purple, and red shown in FIG. 6 represent high-low-energy curves for the base materials having four different atomic numbers, respectively.

However, in conjunction with FIG. 6, only the atomic number or substance type of a single pure material can be determined, and if there are two or more substances overlapped along the propagation path of X-ray, there may be errors in the result of substance recognition according to this method, or even a completely wrong result is acquired. This is the greatest drawback of a conventional dual-energy X-ray substance recognition algorithm. This problem can be solved by the technology of the embodiments of the present disclosure.

After a high-low-energy database for single base materials is established and high-low-energy curves for different base materials are depicted, at steps S412 and S422, in an embodiment of the present disclosure, the base material modules of the above different materials may be further combined for every two of them and placed in an overlapped manner. In other words, high-low-energy projection data of two different base materials overlapped with different thicknesses are collected. Such projection data can be denoted as:

$$p_{1\_ij} = -\ln \int D_1(E) \cdot e^{-\left(\mu_{m_i}(E) \cdot M_i + \mu_{m_j}(E) \cdot M_j\right)} dE \quad (5)$$

$$p_{2\_ij} = -\ln \int D_2(E) \cdot e^{-\left(\mu_{m_i}(E) \cdot M_i + \mu_{m_j}(E) \cdot M_j\right)} dE \quad (6)$$

where, i,j denotes a category number for any two base materials.

The above dual-material projection data calculation equations (5-6) can be approximated by following quadratic surface equation:

$$F = \frac{a_0 + a_1 M_i + a_2 M_j + a_3 M_i^2 + a_4 M_j^2 + a_5 M_i M_j}{1 + b_1 M_i + b_2 M_j} \quad (7)$$

where, F denotes low-energy or high-energy projection data while $a_0$~$a_5$, $b_0$~$b_2$, denotes a constant coefficient to be determined; the physical meaning of the equation (7) is that for two combined, overlapped base materials with different thicknesses, their high-low-energy projection data may be approximately calculated based on the rational fraction defined according to the equation (7), without the knowledge of their respective mass attenuation coefficients as required by the equations (5-6). It is to be noted that surface equations similar to the equation (7) but with a higher order, such as an order of 3 or 4, may be used for approximation. However, the higher the order is, the greater the number of coefficients to be determined is. This should be determined based on the application needs.

Currently, the substance recognition is achieved based on the measured high-low-energy projection data. Therefore, a reverse operation of the equation (7) is to be solved. In other words, the mass thicknesses of different base materials should satisfy the following equations:

$$M_i = \frac{a_{0\_i} + a_{1\_i}p_1 + a_{2\_i}p_2 + a_{3\_i}p_1^2 + a_{4\_i}p_2^2 + a_{5\_i}p_1 \cdot p_2}{1 + b_{1\_i}p_1 + b_{2\_i}p_2} \quad (8)$$

$$M_j = \frac{a_{0\_j} + a_{1\_j}p_1 + a_{2\_j}p_2 + a_{3\_j}p_1^2 + a_{4\_j}p_2^2 + a_{5\_j}p_1 \cdot p_2}{1 + b_{1\_j}p_1 + b_{2\_j}p_2} \quad (9)$$

where, $M_i$,$M_j$ denotes the mass thickness of the base materials with numbers of i,j, while $a_{0\_i/j}$~$a_{5\_i/j}$,$b_{0\_i/j}$~$b_{2\_i/j}$ denotes coefficients to be determined in the surface fitting equation for the i/j$^{th}$ base materials. At step S423, an equation for calculating a surface density of dual base materials in different combinations is established by surfacing fitting.

The equations (8-9) serve for the purpose as follows: for high-low-energy projection data collected with any two overlapped base materials, the equations (8-9) may be used to calculate the accurate mass thicknesses of the two base materials, and once the mass thicknesses of the two base materials are acquired, the projection data corresponding to the thicknesses of the two base materials can be calculated, respectively. In other words, the stratified imaging can be achieved. To achieve the above object, a series of coefficients $a_{0\_i/j}$~$a_{5\_i/j}$,$b_{0\_i/j}$~$b_{2\_i/j}$ to be determined in the equations (8-9) is first required to be determined:

(1) Based on the content in a dashed block on the right of FIG. 4, the step models of single base materials as shown in FIG. 3 are combined for each pair of them and located in an overlapped manner. After that, a high-low-energy X-ray DR scan is performed, and projection data is collected, to establish a high-low-energy projection database for any two overlapped base materials.

(2) The high-low-energy projection data collected for any group of dual overlapped materials is substituted into the equations (8-9) to establish an equation system corresponding to this pair of base materials with different mass thicknesses. This equation system is an one-dimensional linear equation system. With a linear fitting algorithm (for example, the least square fitting method), the values of the series of coefficients $a_{0\_i/j}$~$a_{5\_i/j}$,$b_{0\_i/j}$~$b_{2\_i/j}$ can be calculated conveniently. At this point, all coefficients in the equations (8-9) can be determined completely.

Below, with a group of high-low-energy projection data, a detailed description of the whole procedure of a dual-energy X-ray imaging based on the layered materials according to FIG. 4 is given.

At step S431, a dual-energy X-ray DR scan is performed on an object to be scanned. For any group of high-low-energy projection data ($p_1$,$p_2$) that are collected, it will be substituted into a lookup table of single base material to determine ($p_1$,$p_2$) its coordinate location in "the high-low dual-energy curve of single pure material step" of FIG. 6. Based on its location, the combination of the two base materials corresponding to this point is preliminarily determined by calculating the distances from this point to curves for different base materials.

At step S432, if it is determined that ($p_1$,$p_2$) corresponds to a single base material, then it will be substituted directly into the lookup table of single base materials to recognize its material; however, for most of the cases, ($p_1$,$p_2$) will be determined as a combination of two base materials, and it is assumed that the numbers of these two base materials are i,j.

At step S433, ($p_1$,$p_2$) is substituted into the high-low-energy projection database for the two overlapped base materials with numbers of i,j, that is, into the equations (8-9), to calculate the mass thickness $M_i$,$M_j$ corresponding to the two base materials. At step S434, since the mass attenuation coefficients for the high-energy and low-energy X-rays corresponding to the two base materials are known, the high-low-energy projection data $(p_1,p_2)_{M_i}, (p_1,p_2)_{M_j}$ corresponding to the two materials are calculated, respectively.

At step S435, the high-low-energy projection data $(p_1,p_2)_{M_i}, (p_1,p_2)_{M_j}$ corresponding to $(p_1,p_2)$ and decomposed for the two base materials is re-substituted into the lookup table of single base material for material recognition, and the final result of stratified imaging is acquired.

It is to be noted that: no matter which group of materials are used for distinguishing the features, that is, different categorizing curve methods, such as, the R-curve method, the high-low-energy curve method, a-curve method, or the like, are equivalent mathematically. As long as boundaries among various categories are determined, the material recognition can be performed on actual data. Therefore, although the method of the embodiments of the present disclosure is introduced with reference to the high-low-energy curve method only, its application is not limited to this method.

At step S436, based on the decomposed result, the material distribution image is rendered in a pseudo-color manner to acquire a final distribution image of the multi-layer materials.

Figure 7A:
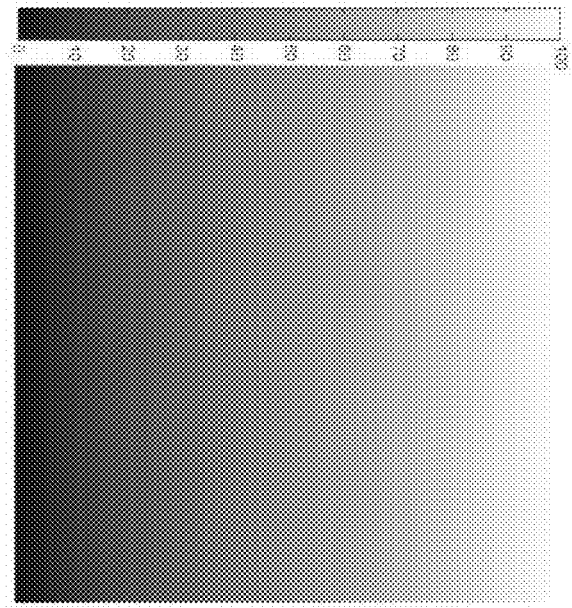
FIGS. 7a, 7b, 7c, 7d, 7e, and 7f are examples of results obtained by simulating the solutions of the embodiments of the present disclosure.
Figure 7B:
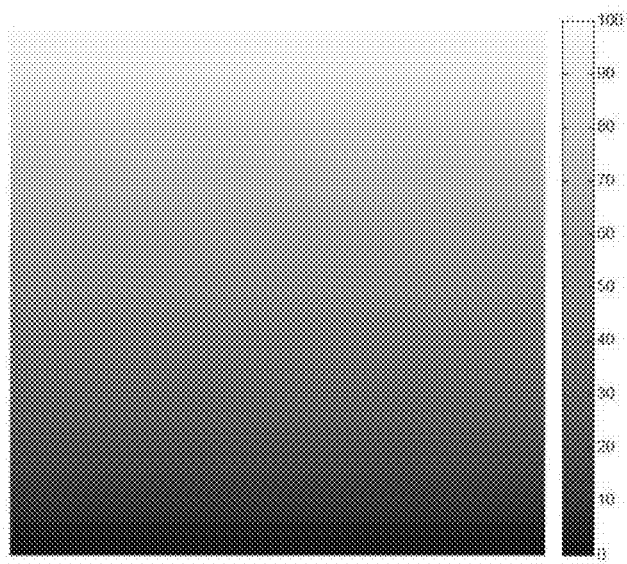
Figure 7C:
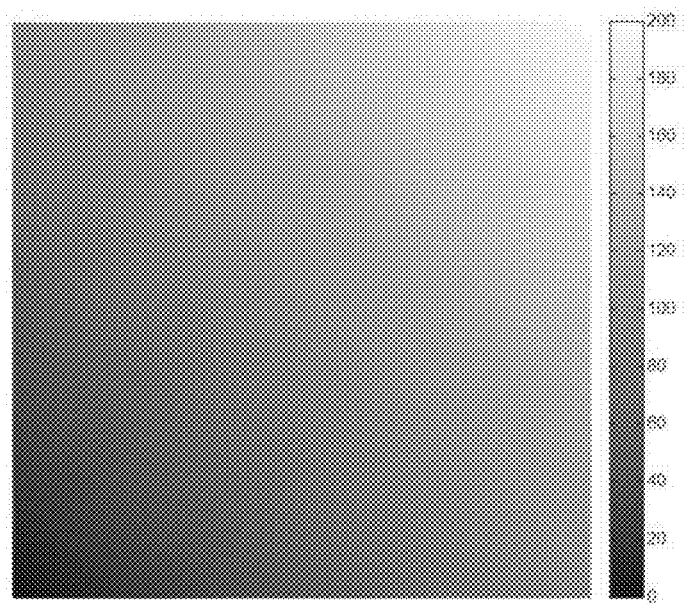
Figure 7D:
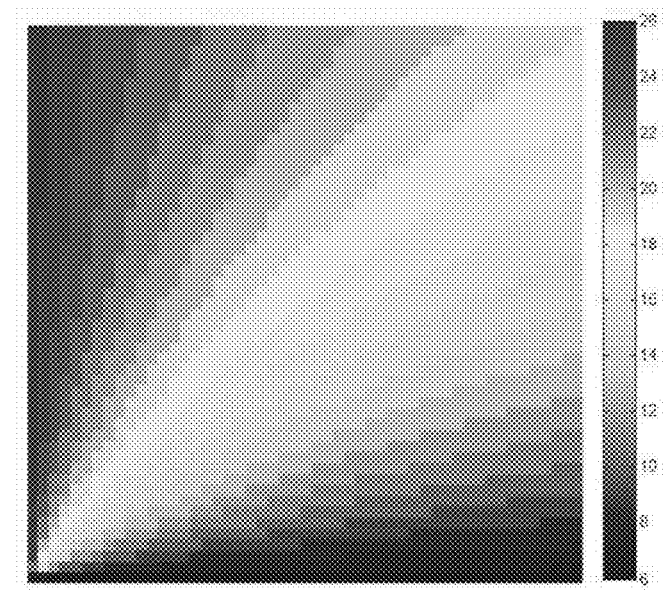
Figure 7E:
Figure 7F:
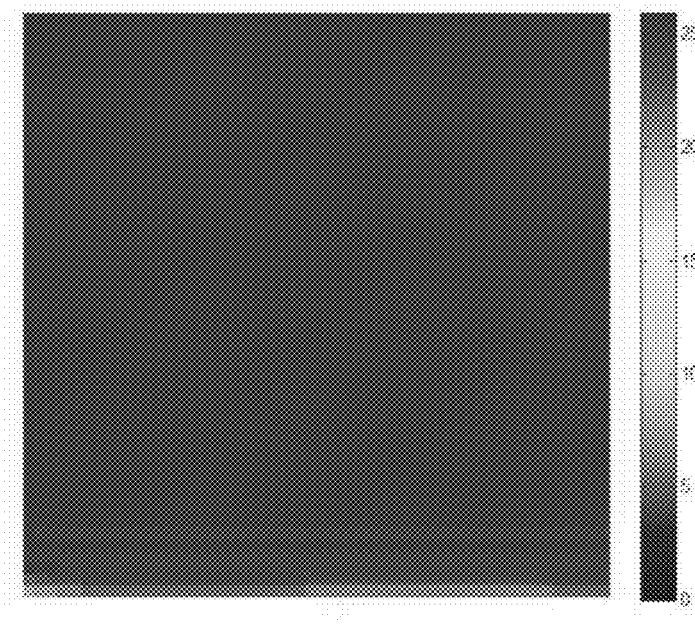
Figure 8A:
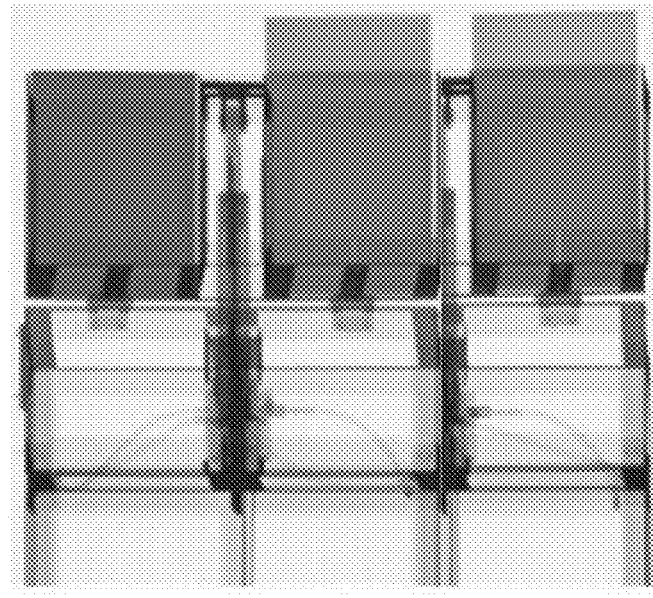
FIGS. 8a, 8b, and 8c are examples of real results obtained according to the solutions of the embodiments of the present disclosure.
Figure 8B:
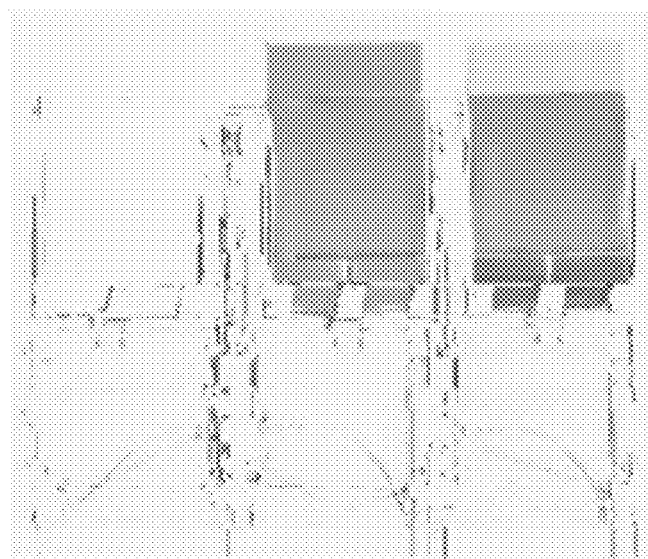
Figure 8C:
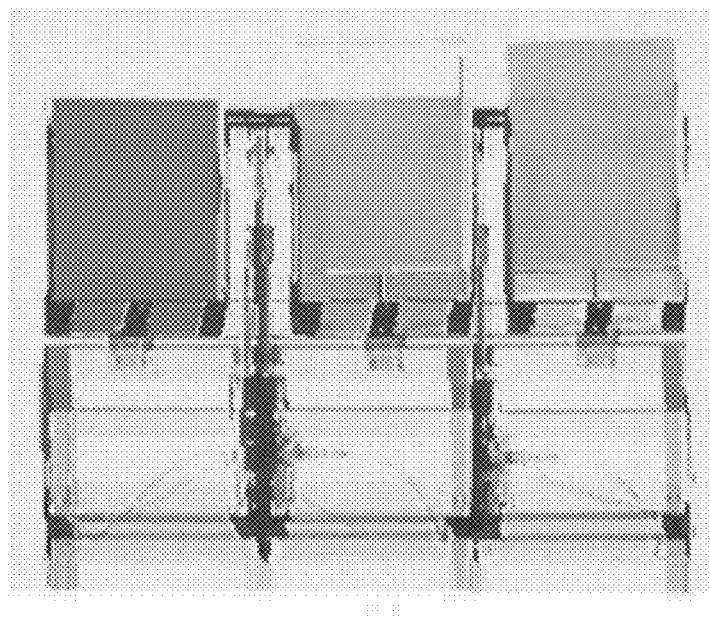

FIGS. 7a-f are examples of results obtained by simulating the solutions of the embodiments of the present disclosure; and FIGS. 8a-c are examples of real results obtained according to the solutions of the embodiments of the present disclosure.

By using a Monte-Carlo method to simulate a dual-energy X-ray energy spectrum for a 6/9 M accelerator, a dual-material stratified imaging for a dual-material step model of graphite and iron is simulated and verified. First, by using a Monte-Carlo simulation software, X-ray energy spectrums of 6 M and 9 M accelerators with a tungsten target is calculated and acquired, and by looking up in a table, X-ray mass attenuation coefficients of the two elements, graphite and iron, are acquired. Next, a step model made of single materials of graphite and iron as shown in the first row of FIG. 7 is designed. FIG. 7a is a step model of graphite material with its mass thickness increasing from left to right and from 0 to 100 in an equally spaced manner. FIG. 7b is a step model of iron material with its mass thickness decreasing from top to bottom and from 100 to 0. FIG. 7c is a result of overlapping the two step models as shown in FIG. 7a and FIG. 7b, and its mass thickness increases progressively from bottom left to upper right and from minimum of 0 to 200. For the three step models of FIGS. 7a, 7b, and 7c, their high-low-energy projection data under the 6 M and 9 M X-ray energy spectrums are calculated, respectively. Displayed in FIGS. 7d, 7e, and 7f are results of substance recognition with the above dual-energy projection data. FIG. 7d shows results of substance recognition by not utilizing the technology of the embodiments of the present disclosure and by directly substituting the dual-energy projection data into the single material high-low-energy curves. The color bar on the right is a color bar corresponding to different atomic numbers. It can be observed that, except for the pure material graphite with z=6 on the bottom row and the pure material iron with z=26 on the left column, all other regions in which the two materials, graphite and iron, are overlapped are incorrectly recognized as an intermediate material with an atomic number of 6<Z<26. FIGS. 7e and 7f shows results of stratified imaging for two base materials of graphite and iron which is achieved by technology according to the embodiments of the present application. It can be observed that the graphite material is correctly recognized throughout the whole model area, and the iron material model is correct in the most of the areas with some errors for areas at the last few rows on the bottom where the iron material is thinner. In other words, the result of this simulation experiment shows that a good stratified imaging and substance recognition on the two overlapped base materials of graphite and iron can be achieved by the dual-energy X-ray DR imaging according to embodiments of the present disclosure.

In a container dual-energy imaging system having a 4/7 M high-low-energy accelerator as a source, the technology according to embodiments of the present application is verified by real experiments. In this experiment, graphite blocks and iron blocks with different thicknesses are manufactured and placed on an iron holder in both of an overlapping manner and a non-overlapping manner. They are scanned to acquire 4/7 M dual-energy DR data, and the layered material based X-ray dual-energy substance recognition technology according to embodiments of the present disclosure is used for verification. The results are shown in FIGS. 8a, 8b, and 8c. Three different material combinations are placed on the iron holder, and they are, from left to right, a pure material block of iron, an overlapped block of iron and graphite with the graphite being higher, and an overlapped block of iron and graphite with the iron being higher. FIG. 8a shows a result of material recognition by not utilizing the technology according to embodiments of the present disclosure and by directly substituting the dual-energy projection data into the single material high-low-energy curve. It can be observed that the conventional technology can only correctly recognize the pure material module of iron on the most left, the non-overlapped graphite and iron. For the overlapped parts of graphite and iron, its recognition results are incorrectly recognized as green which represents aluminum. In other words, only the single pure material can be recognized and overlapped materials cannot be recognized. Such a result is consistent with the result of the simulation experiment of FIG. 7. FIGS. 8b and 8c show results of material recognition after the two base materials of graphite and iron are stratified by the technology according to embodiments of the present disclosure. It can be observed that, in FIG. 8b which shows a graphite material distribution result, the graphite parts are correctly recognized and no iron material is distributed, and there is only some gray lines for the iron holder. This is an error due to the noise in the data and is acceptable. In FIG. 8c which shows an iron material distribution result, the areas comprising the holder part where the iron material is distributed are all correctly recognized and rendered as blue which represents iron.

Therefore, both of the simulation experiment and the real experiment show that: the technology according to the embodiments of the present disclosure may perform a correct substance recognition on an object in which any two materials are overlapped, eliminate the problem of wrong recognition due to different overlapped materials in the conventional dual-energy X-ray DR imaging technology, and prove the correctness, effectiveness and feasibility.

The above solutions of the present disclosure proposes a layered material based multi-layer dual-energy X-ray imaging technology and no big change is made to the hardware of existing dual-energy X-ray imaging systems. By using a specifically designed base materials or calibration modules of specific materials, a stratified imaging of any combination of two base materials on each X-ray path may be achieved. It is advantageous in that the problem of error recognition of materials due to the two overlapped materials can be eliminated and the stratified imaging of multiple materials can be achieved, thereby improving the accuracy of the substance recognition and reducing the rate of false positive and false negative which is very important to the applications in the field of security check and anti-smuggling.

The above detailed description has already set forth numerous embodiments of the dual-energy ray imaging method and system with reference to the diagrams, flow charts, and/or examples. In the case where the diagrams, flow charts, and/or examples comprise one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the present disclosure may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit equivalently, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the present disclosure may be distributed in various forms of program products, and the exemplary embodiments of the subject matter of the present disclosure may be applicable irrespective of the specific types of signal carrier media for distribution. Examples of the signal carrier media comprise but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the present disclosure is already described with reference to several typical embodiments, it is to be appreciated that the terms used herein are illustrative and exemplary, rather than limiting. Since the present disclosure may be practice in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their equivalents shall be embraced by the claims.

We claim:

1. A dual-energy ray imaging method comprising the steps of:
   performing a dual-energy transmissive scanning on an object to be inspected to acquire high-energy projection data and low-energy projection data for at least a part of the object to be inspected;
   determining whether the high-energy projection data and low-energy projection data correspond to a combination of tow base materials by using a lookup table for single base materials;
   for each pixel that is determined to correspond to a combination of the two base materials, searching a high and low energy projection database for mass thicknesses of the two base materials by using the high-energy projection data and the low-energy projection data according to an equation that is determined by using a surface fitting method, the two base materials comprising a first base material and a second base material;
   calculating a first high and low energy data set corresponding to the first base material and a second high and low energy data set corresponding to the second base material based on respective mass attenuation coefficients and the mass thicknesses of the two base materials; and
   performing a substance recognition by using the first high and low energy data set and second high and low energy data set.

2. The method according to claim 1, wherein the high-energy projection data and the low-energy projection data are brought into the lookup table of single base materials to determine their positions in high-low-energy curves of single pure materials with different thicknesses, and then to determine whether the positions correspond to the two base materials by calculating distances from the positions to the curves for different base materials.

3. The method according to claim 1, further comprising steps of:
   displaying an image of the object to be inspected based on at least one of the high-energy projection data and the low-energy projection data; and
   receiving a user selection of at least part of the image to acquire an area of interest;
   wherein the mass thicknesses of the two base materials are calculated with respect to the area of interest.

4. The method according to claim 1, wherein the high and low energy projection database is created by:
   combining step models of first base material and the second base material in an overlapped manner; and
   a high-low-energy X-ray DR scan to establish a high-low-energy projection database for two overlapped base materials.

5. The method according to claim 1, wherein the step of performing the substance recognition comprises using at least one of an R-curve method, a high-low-energy curve method, and an α curve method.

6. The method according to claim 1, wherein the mass thicknesses of the two base materials are calculated according to quadratic equations:

$$M_i = \frac{a_{0\_i} + a_{1\_i}p_1 + a_{2\_i}p_2 + a_{3\_i}p_1^2 + a_{4\_i}p_2^2 + a_{5\_i}p_1 \cdot p_2}{1 + b_{1\_i}p_1 + b_{2\_i}p_2}$$

$$M_j = \frac{a_{0\_j} + a_{1\_j}p_1 + a_{2\_j}p_2 + a_{3\_j}p_1^2 + a_{4\_j}p_2^2 + a_{5\_j}p_1 \cdot p_2}{1 + b_{1\_j}p_1 + b_{2\_j}p_2}$$

where, $M_i$, $M_j$ denotes the mass thickness of the base materials with numbers of i,j, while $a_{0\_i/j}$~$a_{5\_i/j}$, $b_{0\_i/j}$~$b_{2\_i/j}$ denotes coefficients to be determined in the surface fitting equation for the $i/j^{th}$ base materials.

7. A dual-energy ray imaging system comprising:
   a scanning device configured to perform a dual-energy transmissive scan on an object to be inspected to acquire high-energy projection data and low-energy projection data for at least a part of the object to be inspected;
   a data processing device configured to determine whether the high-energy projection data and low-energy projection data correspond to a combination of two base materials by using a lookup table for single base materials, for each pixel that is determined to correspond to a combination of the two base materials, search a high and low energy projection database for mass thicknesses of the two base materials by using the high-energy projection data and the low-energy projection data according to an equation that is determined by using a surface fitting method, the two base materials comprising a first base material and a second base material, further configured to calculate a first high and low energy data set corresponding to the first base material and a second high and low energy data set corresponding to the second base material based on respective mass attenuation coefficients and the mass thicknesses of the two base materials; and configured to perform a substance recognition by using the first high and low energy data set and second high and low energy data set.

8. The dual-energy ray imaging system according to claim 7, further comprising:
 a display device configured to display an image of the object to be inspected based on at least one of the high-energy projection data and the low-energy projection data; and
 an input device configured to receive a user selection of at least part of the image to acquire an area of interest;
 wherein the mass thicknesses of the two base materials are calculated with respect to the area of interest.

9. The dual-energy ray imaging system according to claim 7, wherein the data processing device is further configured to created the high and low energy projection database by:
 combining step models of the first base material and the second base material in an overlapped manner; and
 performing a high-low-energy X-ray DR scan to establish a high-low-energy projection database for two overlapped base materials.

10. A non-transitory computer-readable medium comprising computer-executable instructions for causing one or more processors and/or memory to perform a method comprising the steps of:
 performing a dual-energy transmissive scanning on an object to be inspected to acquire high-energy projection data and low-energy projection data for at least a part of the object to be inspected;
 determining whether the high-energy projection data and low-energy projection data correspond to a combination of two base materials by using a lookup table for single base materials;
 for each pixel that is determined to correspond to a combination of the two base material, searching a high and low energy projection database for mass thicknesses of two base materials by using the high-energy projection data and the low-energy projection data according to an equation that is determined by using a surface fitting method, the two base materials comprising a first base material and a second base material;
 calculating a first high and low energy data set corresponding to the first base material and a second high and low energy data set corresponding to the second base material based on respective mass attenuation coefficients and the mass thicknesses of the two base materials; and
 performing a substance recognition by using the first high and low energy data set and second high and low energy data set.

11. The method according to claim 5, wherein the coefficients are determined by a linear fitting algorithm.

* * * * *